(12) United States Patent
Schäfer et al.

(10) Patent No.: US 6,204,385 B1
(45) Date of Patent: Mar. 20, 2001

(54) PROCESS FOR PREPARING AMIDINES

(75) Inventors: Bernd Schäfer, Dierbach; Thomas Zierke, Böhl-Iggelheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/254,003

(22) PCT Filed: Aug. 21, 1997

(86) PCT No.: PCT/EP97/04548

§ 371 Date: Mar. 1, 1999

§ 102(e) Date: Mar. 1, 1999

(87) PCT Pub. No.: WO98/09950

PCT Pub. Date: Mar. 21, 1998

(30) Foreign Application Priority Data

Sep. 3, 1996 (DE) ................................................ 196 35 674

(51) Int. Cl.$^7$ ........................ C07D 401/12; C07D 271/08
(52) U.S. Cl. ........................ 546/279.1; 548/131; 548/240; 546/286; 546/332; 564/225; 564/244; 564/245
(58) Field of Search .................................. 546/279.1, 286, 546/332; 548/131, 240; 564/225, 244, 245

(56) References Cited

PUBLICATIONS

Berichte, 18, 1998, 2845–55.
Schnur, *J. Org. Chem.*, 44(18), 1979, 3726–29.
Barker et al., *J. Org. Chem.*, 46(9), 1981, 2455–65.
Nii et al., *Tetra. Letters*, 27, 1979, 2517–2520.
Jendralla et al. *Tetrahedron*, 51(44), 1995, 12047–68.
Moser et al., *Helv. Chim. Acta*, vol. 69, 1986, 1224–62.
Gour–Salin et al., *Can. J. Chem.*, vol. 69, 1991, 1288–97.
Srivastava et al., *J. Med. Chem.*, 27(3), 1984, 266–269.

*Primary Examiner*—Charanjit S. Aulakh
(74) *Attorney, Agent, or Firm*—Keil & Weinkauf

(57) ABSTRACT

A process for preparing amidines and their salts with inorganic or organic acids comprises reacting the corresponding nitrile with ammonia, $C_1$–$C_6$-alkylamine or hydrazine in the presence of a mercaptocarboxylic acid and in the presence or absence of an in-organic or organic ammonium salt.

2 Claims, No Drawings

PROCESS FOR PREPARING AMIDINES

This application is a 371 of PCT/EP97/04548 Aug. 21, 1997 now W/O 98/09950 Mar. 12, 1998.

The present invention relates to a novel process for preparing amidines.

Amidines can be prepared by many routes. One of the best-tried methods is the Pinner reaction followed by ammonolysis of the iminocarboxylic ester (Ber. 18, (1885) 2845). A disadvantage of this method is the two-step reaction. As a rule, a large excess of hydrogen chloride is used, which ultimately gives rise to large amounts of concomitant salts and can sometimes cause separation problems. Finally, the reaction times in this reaction sequence are relatively long and conversions and yields are only moderate. In a manner similar to the Pinner reaction, mercaptans can be employed as auxiliary reagents for preparing amidines (R. C. Schnur, J. Org. Chem. 44, (1979) 3726). One variant of this synthesis is the addition of hydrogen sulfide to nitriles to give thiocarboxamides, followed by alkylation of the sulfur and ammonolysis (H. Rappoport, J. Org. Chem. 46, (1981) 2455; M. Ohno, Tetrahedron Lett. (1979) 2517). In all these cases, extremely malodorous and highly toxic compounds have to be handled. For the alkylation, methyl iodide or dimethyl sulfate are normally used. Both chemicals have been shown to be potent carcinogens.

Ammonia can be added directly under pressure in liquid ammonia to heteroaromatic or aromatic nitriles, but, this requires long reaction times (16 h) and gives only poor product yields (40%) (P. C. Srivastava, J. Med. Chem. 27, (1984) 266). Amidines can further be synthesized from nitriles by reaction with hydroxylamine and reductive cleavage of the intermediate carboxamide oximes (H. Jendralla, Tetrahedron 51, (1995) 12047). The reductive cleavage, however, considerably limits the substitution pattern of the nitrile. Double bonds or nitro groups are likewise easily hydrogenated. Protecting groups, for example the benzyl group, are also easily cleaved.

In 1986, A. Eschenmoser published a cysteine-catalyzed amidine synthesis (Helv. Chim. Acta 69, (1986) 1224). However, the experimental examination of this synthesis showed the yield to be only about 58%.

The simplest synthesis of amidines is the direct addition of ammonia to nitrites. Studies with substituted nitrites showed, however, that there is limited conversion even under pressure and that the amidine yield is therefore correspondingly low.

It is an object of the present invention to develop a simple method by which it is possible to convert even nitrites having complicated substitution patterns, which cannot be used by conventional amidine synthesis, into the corresponding amidines.

We have found that this object is achieved by to a process for preparing amidines and their salts with inorganic or organic acids, which comprises reacting the corresponding nitrile with ammonia, a $C_1$–$C_6$-alkylamine or hydrazine in the presence of a mercaptocarboxylic acid carrying, apart from the SH and the COOH groups, no other groups reactive under the reaction conditions, and in the presence or absence of an inorganic or organic ammonium salt.

By this process, virtually all amidines of the formula I

R—C(NHR')=NH  (I)

where R is an aliphatic, aromatic or heterocyclic radical and R' is a hydrogen atom, a $C_1$–$C_6$-alkyl radical or an amino group, can be prepared.

In the formula I, R can be a derivative of benzene, for example phenyl, o-fluorophenyl, m-fluorophenyl, p-fluorophenyl, o-chlorophenyl, m-chlorophenyl, p-chlorophenyl, o-nitrophenyl, m-nitrophenyl, p-nitrophenyl, o-methoxyphenyl, m-methoxyphenyl or p-methoxyphenyl.

R can further be a heterocyclic system, in particular a derivative of pyridine, pyrimidine, thiophene, furan, pyrrole, isoxazole, 1,2,4-oxadiazole, pyrroline or pyrrolidine, for example pyridin-2-yl, pyridin-3-yl, pyridin-4-yl, isoxazol-3-yl, 1,2,4-oxadiazol-3-yl, pyrimidin-2-yl, pyrimidin-4-yl or thiophen-2-yl.

Of the rings mentioned, the pyridine ring is preferred, in particular when substituted in the 2-position by a cyano group. Preference is also given to the isoxazole ring with a cyano function in the 3-position and to the 1,2,4-oxadiazole ring with a cyano function in the 3-position.

Finally, R can also be an oligopeptide structure consisting of up to 12 natural amino acids, the corresponding D-amino acids or compounds which are very similar to natural amino acids. Specifically, these are the following amino acids: glycine, alanine, phenylalanine, proline, valine, 2,3-, 3,4- or 4,5-dehydroproline, cyclohexylalanine.

The process is of very particular interest for preparing the recently published thrombin inhibitors carrying an amidine radical, which are mentioned for example in the patent applications WO 94/29335, WO 94/29336, WO 95/23609, EP 669,317 and WO 95/35309. Most of them have the structure below:

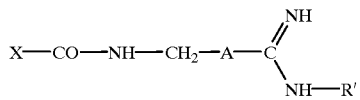

where X is the radical of a substituted or unsubstituted amino acid, preferably proline or dehydroproline, and

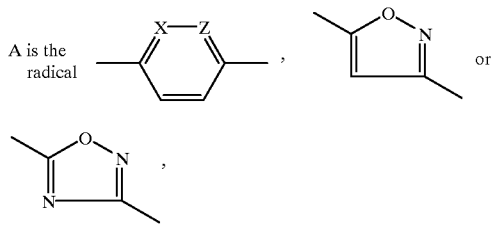

where
Y and Z are CH or NH groups.

Asymmetric centers in the compounds of the formula I do not interfere with the reaction and remain unaffected by the reaction.

The reaction is carried out in an inert solvent, preferably in solvents in which the solubility of ammonia at 0° C. and 1 bar is more than 2% by weight. Such solvents are in particular alcohols, such as methanol and ethanol. The same considerations are applicable for the use of amines and hydrazine.

The reaction is generally carried out at a temperature in the range from –10 to 200° C. and at a pressure in the range from 1 to 20 bar. Preference is given to the boiling point of the reaction mixture and 1 bar. The reaction is very particularly preferably carried out at autogenous pressure. Carrying out the reaction without employing superatmospheric pressure requires occasional resaturation with ammonia or amines.

The reaction can be carried out in the presence of an ammonium salt. This generally affords the corresponding amidinium salts. If an ammonium salt is used, this should be the salt of an acid which is stronger than the mercaptocarboxylic acid used. Specifically, these are the salts of the hydrohalic acids (in particular hydrochloric acid), sulfuric acid, phosphoric acid, nitric acid and $C_{1-6}$-carboxylic acids.

Preferably, however, the reaction is carried out in the absence of an ammonium salt. In this case, the reaction product is the amidinium salt of the mercaptocarboxylic acid. In addition to the catalytic effect, the mercaptocarboxylic acid also exercises a stabilizing action on the amidine. In the reaction, the mercaptocarboxylic acid is generally employed in an amount of from 0.05 to 5 mol, preferably about 1 mol per mole of nirile.

A particular advantage of mercaptocarboxylic acids is that they have little, if any, odor, while the processes described in the literature often require malodorous and highly toxic substances.

Suitable mercaptocarboxylic acids are those not carrying any other reactive groups apart from the SH and the COOH groups. These are in particular those of the formula HS-R'-COOH where R' is a $C_{1-12}$-alkylene radical and where the hydrocarbon chain contains up to 3 rings and may be substituted or interrupted by heteroatoms which are inert under the reaction conditions, such as nitrogen and oxygen. Preferably, R' is a $C_{1-6}$-alkylene radical or a phenylene group which may be mono- or disubstituted by the following radicals: methyl, methoxy, ethoxy, n-propoxy, i-propoxy, $C_{1-6}$-alkylamino, $C_{1-6}$-dialkylamino, halogen, nitro.

Specifically, these are mercaptoacetic acid, α- and β-mercaptopropionic acid, N-acylated aminothiocarboxylic acids—such as N-acylated cysteines—, mercaptoalkyleneprolines—such as N-(3-mercaptopropyl)proline—, mercaptoalkanoylprolines—such as N-(3-mercaptopropionyl)proline—, or cyclic thiocarboxylic acids — such as mercaptobenzoic acid.

Captopril and acetylcysteine have proved to be particularly advantageous for the process.

Generally, the reaction is terminated in a customary manner when no more nitrile can be detected (for example by GC, HPLC, TLC) in the reaction mixture.

Work-up to isolate the product is normally carried out by conventional methods, such as distillation, filtration, centrifugation or extraction.

The process according to the invention can be carried out batch-wise, for example in a stirred tank reactor. The simplicity of the process has the advantage that it can be adapted to continuous operation, for example by using a tubular reactor or a stirred tank reactor cascade.

The stereochemistry of the mercaptocarboxylic acids is of no importance with respect to their effectiveness in the reaction claimed.

The crude products obtained can, if desired, be purified further, for example by crystallization, extraction or chromatography.

Surprisingly, it was found that, when carrying out the process according to the invention, undesirable side reactions do not take place and that the conversion is quantitative if mercaptocarboxylic acids are used.

Example 1: Synthesis of (S)-(3,4-dehydroproline(6-amidino-3-picolinyl) amide [sic] using N-acetyl-(S)-cysteine as catalyst 2.63 g (10 mmol) of (S)-(3,4-dehydroproline(6-cyano-3-picolinyl)-amide [sic] hydrochloride together with 1.79 g (11 mmol) of N-acetyl-(S)-cysteine were intially charged in 10 ml of methanol. At 65° C., the reaction mixture was saturated with ammonia. After 2 h, no more starting material could be detected by thin layer chromatography. The reaction mixture was concentrated using a rotary evaporator. 4.7 g of an almost colorless solid containing 70.5% of the desired product were obtained. M.p.: 66° C., $^{13}$C, NMR [sic] (CDCl$_3$, ppm): 162.1 (amidine).

Example 2: Synthesis of N-((t-butoxycarbonyl)methylene)-(R)-cyclohexylalanyl-(S)-proline(6-amidino-3-picolinyl)amide using N-acetyl-(S)-cysteine as catalyst 50 g (105 mmol) of N-((t-butoxycarbonyl)methylene)-(R)-cyclohexylalanyl-(S)-proline(6-cyano-3-picolinyl) amide together with 17.7 g (109 mmol) of N-acetyl-(S)-cysteine were initially charged in 50 ml of methanol. At 65° C., the reaction mixture was saturated with ammonia. After 4 h, no more starting material could be detected by thin layer chromatography. The reaction mixture was concentrated using a rotary evaporator. 70.3 g of an almost colorless solid containing 75.3% of N-((t-butoxycarbonyl)methylene)-(R)-cyclohexylalanyl-(S)-proline(6-amidino-3-picolinyl)amide were obtained, $^{13}$C-NMR (CDCl$_3$, ppm): 162.3 (amidine).

Example 3: Synthesis of N-Boc-N-((t-butoxycarbonyl)methylene)-(R)-cyclohexylalanyl-(S)-(3,4-dehydroproline(6-amidino-3-picolinyl)amide [sic] using N-acetyl-(S)-cysteine as catalyst 124.3 g (197 mmol) of N-Boc-N-((t-butoxycarbonyl)methylene)-(R)-cyclohexylalanyl-(S)-(3,4-dehydroproline(6-cyano-3-picolinyl)amide [sic] together with 35.5 g (218 mmol) of N-acetyl-(S)-cysteine were initially charged in 400 ml of methanol. At 65° C., the reaction mixture was saturated with ammonia. After 6.5 h, no more starting material could be detected by thin layer chromatography. The reaction mixture was concentrated using a rotary evaporator. 165.2 g of an almost colorless solid containing 81.6% of N-Boc-N-((t-butoxycarbonyl)methylene)-(R)-cyclohexylalanyl-(S)-(3,4-dehydroproline(6-amidino-3-picolinyl)amide [sic] were obtained, m.p.: 91–118° C. (decomposition). MS (EI): 612.4 g/mol.

Example 4: Synthesis of N-((t-butoxycarbonyl)methylene)-(R)-cyclohexylalanyl-(S)-(3,4-dehydroproline (6-amidino-3-picolinyl)amide [sic] using N-acetyl-(S)-cysteine as catalyst 2.5 g (5 mmol) of N-((t-butoxycarbonyl)methylene)-(R)-cyclo-hexylalanyl-(S)-(3,4-dehydroproline(6-cyano-3-picolinyl)amide [sic] together with 0.89 g (5.5 mmol) of N-acetyl-(S)-cysteine were initially charged in 6 ml of methanol. At 65° C., the reaction mixture was saturated with ammonia. After 5 h, no more starting material could be detected by thin layer chromatography. The reaction mixture was concentrated using a rotary evaporator. 3.3 g of an almost colorless solid containing 73.6% of N-((t-butoxycarbonyl) methylene)-(R)-cyclohexylalanyl-(S)-(3,4-dehydroproline(6-amidino-3-picolinyl)amide [sic] were obtained.

Example 5: Synthesis of N-((t-butoxycarbonyl)methylene)-(R)-cyclohexylalanyl-(S)-proline(6-amidino-3-picolinyl)amide using mercaptoacetic acid as catalyst 5 g (10.5 mmol) of N-((t-butoxycarbonyl)methylene)-(R)-cyclohexylalanyl-(S)-proline(6-cyano-3-picolinyl) amide together with 1.1 g (12 mmol) of mercaptoacetic acid were initially charged in 10 ml of methanol. At 25° C., the reaction mixture was saturated with ammonia. After 4 h, no more starting material could be detected by thin layer chromatography. The reaction mixture was concentrated using a rotary evaporator. 6.3 g of a green solid containing 70% of N-((t-butoxycarbonyl)methylene)-(R)-cyclohexylalanyl-(S)-proline(6-amidino-3-picolinyl)amide were obtained.

Example 6: Synthesis of N-Boc-N-((t-butoxycarbonyl)methylene)-(R)-cyclohexylalanyl-(S)-(3,4-dehydroproline (6-amidino-3-picolinyl)amide [sic] using N-((R)-3-mercaptoisobutanoyl)-(S)-proline (captopril) as catalyst 3 g (5 mmol) of N-Boc-N-((t-butoxycarbonyl)methylene)-(R)-cyclohexylalanyl-(S)-(3,4-dehydroproline (6-cyano-3-picolinyl)amide [sic] together with 1.21 g (5.5 mmol) of N-((R)-3-mercaptoisobutanoyl)- (S)-proline were initially charged in 8 ml of methanol. At 65° C., the reaction mixture was saturated with ammonia. After 4 h, no more starting material could be detected by thin layer chromatography. The reaction mixture was concentrated using a rotary evaporator. 4.1 g of an almost colorless solid containing 54.9% of N-Boc-N-((t-butoxycarbonyl)methylene)-(R)-cyclohexylalanyl-(S)-(3,4-dehydroproline(6-amidino-3-picolinyl)amide [sic] were obtained, MS (EI): 612.4 g/mol.

13C—NMR [sic] ($CDCl_3$, ppm): 162.1 (amidine).

Example 7: Synthesis of Boc-(R)-cyclohexylalanyl-(S)-proline-(6-amidino-3-picolinyl)amide using N-acetyl-(S)-cysteine as catalyst 5 g (10.5 mmol) of Boc-(R)-cyclohexylalanyl-(S)-proline (6-cyano-3-picolinyl)amide together with 1.7 g (10.5 mmol) of N-acetyl-(S)-cysteine were initially charged in 20 ml of methanol. At 65° C., the reaction mixture was saturated with ammonia. After 5 hours, no more starting material could be detected by thin layer chromatography. After stirring overnight, the reaction mixture was concentrated using a rotary evaporator. 7 g of an almost colorless solid containing 78.3% of Boc-(R)-cyclohexylalanyl-(S)-proline(6-amidino-3-picolinyl)amide were obtained, $^{13}$C-NMR ($CDCl_3$, ppm): 162.3 (amidine).

The following compounds were synthesized by the method of Example 1:

Example 8: N-(1,3-dihydroxypropan-2-yl)-(R)-cyclohexylglycyl-(S)-proline(6-amidino-3-picolinyl)amide $^{13}$C-NMR (DMSO, ppm): δ=162.3 (amidine), FAB-MS: $(M+H)^+$=461.

Example 9: N-Boc-N-((t-butoxycarbonyl)ethylene)-(R)-cyclohexyl-alanyl-(S)-proline(6-amidino-3-picolinyl)amide $^{13}$C-NMR (DMSO, ppm): δ=161.9 (amidine), FAB-MS: $(M+H)^+$=629.

Example 10: N-Boc-N-((t-butoxycarbonyl)methylene)-(R)-cyclohexyl-alanyl-1-aminocyclopropane-1-(6-amidino-3-picolinyl)carboxamide $^{13}$C-NMR (DMSO, ppm): δ=162.2 (amidine), FAB-MS: $(M+H)^+$=601.5.

Example 11: N-(6-Amidinopyridin-3-ylmethyl)-2-(2-oxo-3-phenylmethanesulfonylaminopyrrolidin-1-yl)acetamide

FAB-MS: $(M+H)^+$=445.

Example 12: N[(t-butoxycarbonyl)methylene]-N-Boc-(R)-cyclohexylalanyl-(S)-N-methylalanine(6-amidino-3-picolinyl)amide

FAB-MS: $(M+H)^+$=603.

Example 13: N[(t-butoxycarbonyl)methylene]-N-benzylglycyl-(S)-3,4-dehydroproline(6-amidino-3-picolinyl)amide

FAB-MS: $(M+H)^+$=507.

Example 14: N-Boc-N-[(butoxycarbonyl)methylene]-(R)-cyclohexylalanyl-(S)-(3,4-dehydroproline(6-(N-methyl)amidino-3-picoli-nyl)amide [sic]

FAB-MS: $(M+H)^+$=626.6.

Example 15: N-Boc-N-[(t-butoxycarbonyl)methylene]-(R)-cyclohexylalanyl-(S)-(3,4-dehydroproline(6-(N-amino)amidino-3-picolinyl)amide [sic]

FAB-MS: $(M+H)^+$=627.6.

Example 16: N-Boc-N-[(t-butoxycarbonyl)methylene]-(R)-cyclohexylalanyl(4,4-dimethyl)proline(6-amidino-3-picolinyl)amide

FAB-MS: $(M+H)^+$=642.7.

Example 17: N-Boc-N-[(t-butoxycarbonyl)methylene]-(R)-cyclohexylalanyl-(S)-(3,4-dehydroproline(3-amidinoisoxazol-5-yl)methylamide [sic]

FAB-MS: $(M+H)^+$=602.7.

Example 18: 3-amidino-5-N-Boc-aminomethyl-1,2,4-oxadiazole

FAB-MS: $(M+H)^+$=242.

Example 19: 3-(2-trifluoromethylbenzyl)benzoyl-(5)-3,4-dehydroproline(6-amidino-3-picolinyl)amide acetate White crystals, mp. 188–191° C., FAB-MS: $(M+H)^+$= 508.

Example 20: 9-hydroxyfluorenyl-9-carboxy-(S)-3,4-dehydroproline-(6-amidino-3-picolinyl)amide acetate White crystals, mp. 181–185° C. (decomposition), FAB-MS: $(M+H)^+$=454.

Example 21: N-methylsulfonyl-(R)-cyclohexylalanyl-(S)-3,4-dehydroproline(6-amidino-3-picolinyl)amide acetate White crystals, mp. 175–176° C., FAB-MS: $(M+H)^+$= 477.

Comparative experiment with ammonia without catalyst

In a 300 ml autoclave, 10 g (21 mmol) of Boc-(R)-cyclohexylalanyl-(S)-proline(6-cyano-3-picolinyl)amide and 2.25 g (42 mmol) of ammonium chloride in 100 ml of methanol together with 60 ml of liquid ammonia were initially charged and adjusted to an internal pressure of 40 bar by applying pressurized nitrogen. After a reaction time of 100 h at 30° C., the reaction mixture was concentrated using a rotary evaporator. By HPLC, the yield of Boc-(R)-cyclohexylalanyl-(S)-proline(6-amidino-3-picolinyl)amide was only 48.5%.

Comparative experiment using cysteine as catalyst 10 g (21 mmol) of Boc-(R)-cyclohexylalanyl-(S)-proline (6-cyano-3-picolinyl)amide together with 2.25 g of ammonium chloride and 2.54 g (21 mmol) of (S)-cysteine were initially charged in 100 ml of methanol. At 20–30° C., the reaction mixture was saturated with ammonia. After 1.5 h, no more starting material could be detected by thin layer chromatography. After stirring overnight, the reaction mixture was concentrated using a rotary evaporator. 15 g of an almost colorless solid containing 40% Boc-(R)-cyclohexylalanyl-(S)-proline(6-amidino-3-picolinyl)amide by HPLC were obtained.

We claim:

1. A process for preparing amidines and their salts with inorganic or organic acids, which comprises reacting the corresponding nitrile with ammonia, a $C_1$–$C_6$-alkylamine or hydrazine in the presence of a mercaptocarboxylic acid carrying, apart from the SH and the COOH groups, no other groups reactive under the reaction conditions, and in the presence or absence of an inorganic or organic ammonium salt.

2. The process as claimed in claim 1, wherein the process is carried out in the absence of an ammonium salt.

* * * * *